(12) United States Patent
Herzig et al.

(10) Patent No.: US 7,294,739 B1
(45) Date of Patent: Nov. 13, 2007

(54) BASIC AMINE ESTERS OR OLEIC ACID AND THEIR USE AS ANTI-INFLAMMATORY OR IMMUNOBODULATORY AGENTS

(75) Inventors: Yaacov Herzig, Raanana (IL); David Lerner, Jerusalem (IL); Jeffrey Sterling, Jerusalem (IL)

(73) Assignee: Teva Pharmacaetical Industries Ltd., Petach-Tikva (IL)

( * ) Notice: Subject to any disclaimer, the term of this patent is extended or adjusted under 35 U.S.C. 154(b) by 0 days.

(21) Appl. No.: 11/594,015

(22) Filed: Nov. 6, 2006

(51) Int. Cl.
C07C 61/00 (2006.01)
A01N 37/00 (2006.01)
(52) U.S. Cl. ...................... 562/400; 514/506
(58) Field of Classification Search ............. None
See application file for complete search history.

(56) References Cited

U.S. PATENT DOCUMENTS

2004/0186072 A1   9/2004   Burstein .................. 514/53
2006/0183797 A1   8/2006   Cohen ..................... 514/546

OTHER PUBLICATIONS

Vavrova, et al., Bioorg. and Med. Chem., 11, 5381-5390 (2003).
Sterling, et al., J. Med. Chem., 45, 5260-5279 (2002).

*Primary Examiner*—Yvonne Eyler
*Assistant Examiner*—M. Louisa Lao
(74) *Attorney, Agent, or Firm*—Merchant & Gould

(57) ABSTRACT

This invention is directed to compounds of the following formula (I):

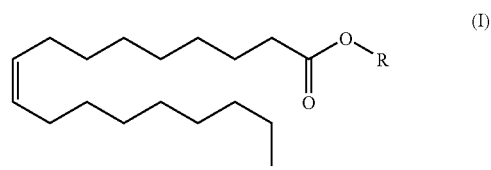

wherein R is either:

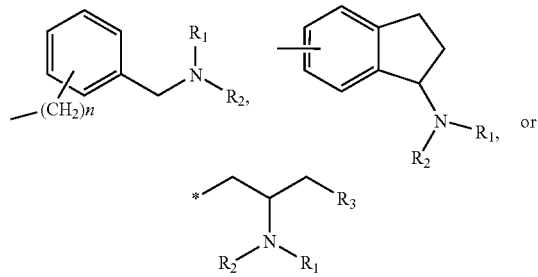

wherein $R_1$ and $R_2$ are as defined in the specification; the use of these compounds for treating inflammatory disorders; and pharmaceutical compositions comprising a therapeutically effective amount of the above-defined compounds.

21 Claims, No Drawings

BASIC AMINE ESTERS OR OLEIC ACID AND THEIR USE AS ANTI-INFLAMMATORY OR IMMUNOBODULATORY AGENTS

FIELD OF THE INVENTION

The present invention relates to novel compounds, pharmaceutical compositions containing said compounds and their use in the treatment of inflammatory disorders.

BACKGROUND OF THE INVENTION

Inflammation is commonly divided into three phases: acute inflammation, the immune response and chronic inflammation. Acute inflammation is the initial response to tissue injury and is mediated by the release of histamine, serotonin, bradykinin, prostaglandins and leukotrienes. The immune response, usually preceded by the acute inflammation phase, occurs when immunologically competent cells are activated in response to foreign organisms or antigenic substances liberated during the acute or chronic inflammatory response. The outcome of the immune response for the host may be beneficial, as when it causes invading organisms to be phagocytosed or neutralized. However, the outcome may be deleterious if it leads to chronic inflammation without resolution of the underlying injurious process as it occurs in rheumatoid arthritis.

The treatment of patients with inflammation envisages the relief of pain, which is the presenting symptom and the major continuing complaint of the patient, as well as the slowing or arrest of the tissue-damaging process.

Anti-inflammatory agents are usually classified as steroidal or glucocorticoids and nonsteroidal anti-inflammatory agents (NSAIDs). The glucocorticoids are powerful anti-inflammatory agents but the high toxicity associated with chronic corticosteroid therapy inhibits their use except in certain acute inflammatory conditions. Although NSAIDs have assumed a major role in the treatment of chronic conditions such as rheumatoid arthritis, they are also associated with various toxicities ranging from gastrointestinal bleeding to life-threatening cardiotoxicity.

PCT application publication number WO 02/083122, hereby incorporated by reference, discloses fatty alcohols and fatty esters useful for treating inflammation. PCT application publication number WO 02/083059, hereby incorporated by reference, discloses uses of esters of long-chained fatty acids for the treatment of autoimmune diseases and other immune-associated inflammatory disorders.

What is needed are novel compounds for treating inflammation that are less toxic to the patient.

SUMMARY OF THE INVENTION

Accordingly, the present invention relates to compounds of formula (I):

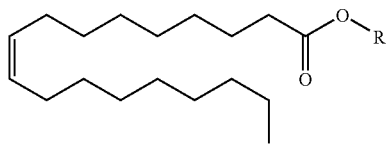

wherein R is either:

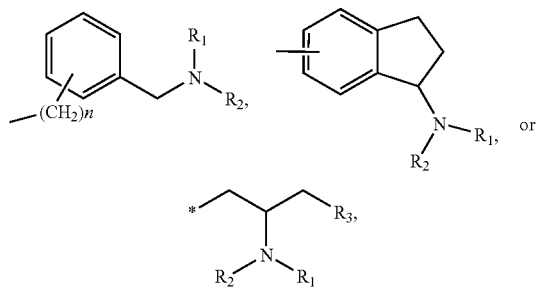

and wherein $R_1$ and $R_2$ are the same or different and are either hydrogen or $C_1$-$C_4$ alkyl, n is 0 or 1, and $R_3$ is unsubstituted phenyl or phenyl substituted with alkyl, alkoxy, hydroxyl, halogen or a pharmaceutically acceptable salt thereof.

The invention also relates to pharmaceutical compositions containing the compounds of formula (I) and their use compositions in the treatment of inflammatory disorders.

DETAILED DESCRIPTION OF THE INVENTION

The present invention includes amine esters of octadecenoic acid and pharmaceutically acceptable salts thereof which are useful for treatment of inflammation. Compounds, pharmaceutical compositions and methods of treatment are provided.

The present invention is directed to compounds of formula (I):

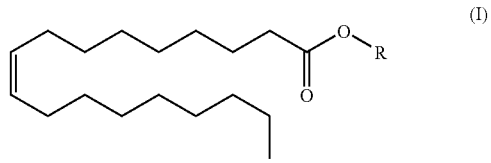

wherein R is either:

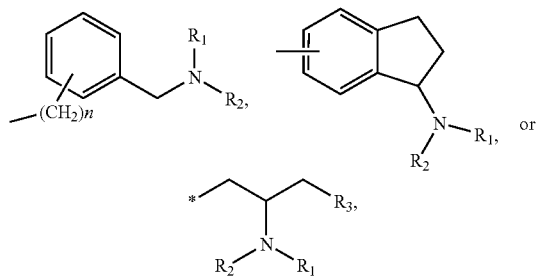

and wherein $R_1$ and $R_2$ are the same or different and are either hydrogen or $C_1$-$C_4$ alkyl, n is 0 or 1, and $R_3$ is unsubstituted phenyl or phenyl substituted with alkyl, alkoxy, hydroxyl, halogen or a pharmaceutically acceptable salt thereof.

In an embodiment of the present invention, the compound of formula (II) is:

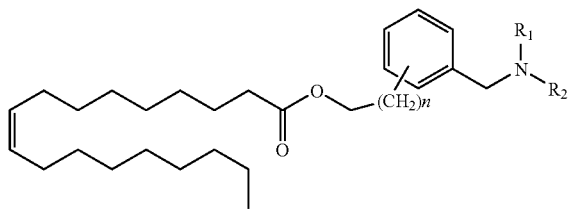

wherein $R_1$ and $R_2$ are each methyl, n is as described above or a pharmaceutically acceptable salt thereof.

In another embodiment of the present invention, the compound is selected from the group consisting of octadec-(Z)-9-enoic acid 4-dimethyl-aminomethyl-benzyl ester and octadec-(Z)-9-enoic acid 4-dimethylaminomethyl-phenyl ester or a pharmaceutically acceptable salt thereof.

In an embodiment of the present invention, the compound of formula (III) is:

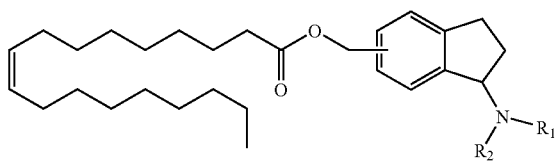

wherein $R_1$ and $R_2$ are defined above.

In another embodiment of the present invention, the compound is selected from the group consisting of octadec-(Z)-9-enoic acid-3-dimethylamino-indan-5-yl ester and octadec-(Z)-9-enoic acid 3-propylamino-indan-5-yl ester or a pharmaceutically acceptable salt thereof.

In an embodiment of the present invention, the compound of formula (IV) is:

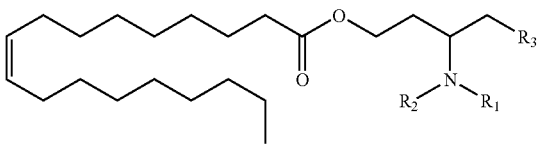

wherein $R_3$ is unsubstituted phenyl, $R_1$ and $R_2$ are each hydrogen, or $R_1$ and $R_2$ are each methyl.

In another embodiment of the present invention, the compound is selected from the group consisting of octadec-(Z)-9-enoic acid 2-amino-3-phenyl-propyl ester and octadec-(Z)-9-enoic acid 2-dimethylamino-3-phenyl-propyl ester or a pharmaceutically acceptable salt thereof.

In the practice of this invention, pharmaceutically acceptable salts include, but are not limited to, the esylate, mesylate, maleate, fumarate, tartrate, hemi-tartarate, hydrochloride, hydrobromide, p-toluenesulfonate, benzoate, acetate, phosphate and sulfate salts.

In various embodiments, halogen includes fluorine, chlorine, bromine, or iodine. Alkyl, alkoxy, etc., include both straight and branched groups; but reference to an individual radical such as "propyl" embraces only the straight chain radical, a branched chain isomer such as "isopropyl" being specifically referred to.

"Alkyl" includes linear alkyls, branched alkyls, and cycloalkyls. Example alkyl groups include: $C_{1-4}$alkyl, such as methyl, ethyl, propyl, isopropyl, butyl, iso-butyl, sec-butyl, tert-butyl; $C_{1-10}$alkyl, such as methyl, ethyl, propyl, isopropyl, butyl, iso-butyl, sec-butyl, tert-butyl, pentyl, 3-pentyl, hexyl, heptyl, octyl, nonyl and decyl; $(C_{3-12})$ cycloalkyl such as cyclopropyl, cyclobutyl, cyclopentyl, cyclohexyl, cycloheptyl, cyclooctyl, bicyclic, or multi-cyclic substituents, such as of the formulas

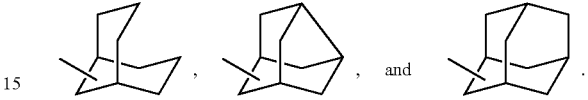

"Alkoxy" includes —O-alkyl in which the alkyl is as described above. Example alkoxys include, but are not limited to: methoxy, ethoxy, n-propoxy, n-butoxy, n-pentoxy, hexyloxy, and heptyloxy.

The carbon atom content of various hydrocarbon-containing moieties is indicated by a prefix designating a lower and upper number of carbon atoms in the moiety, i.e., the prefix $C_{i-j}$ indicates a moiety of the integer "i" to the integer "j" carbon atoms, inclusive. Thus, for example, $(C_1-C_{10})$alkyl or $C_{1-10}$alkyl refers to alkyl of one to ten carbon atoms, inclusive, and $(C_1-C_4)$alkyl or $C_{1-4}$alkyl refers to alkyl of one to four carbon atoms, inclusive.

The compounds of the present disclosure are generally named according to the IUPAC nomenclature system. Abbreviations, which are well known to one of ordinary skill in the art, may be used (e.g., "Ph" for phenyl, "Me" for methyl, "Et" for ethyl, "h" for hour or hours, "g" or "gm" for gram(s), "mL" for milliliters, and "rt" for room temperature).

"About" modifying, for example, the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like proximate considerations. The term "about" also encompasses amounts that differ due to aging of a formulation with a particular initial concentration or mixture, and amounts that differ due to mixing or processing a formulation with a particular initial concentration or mixture. Whether modified by the term "about" the claims appended hereto include equivalents to these quantities.

The indefinite article "a" or "an" and its corresponding definite article "the" as used herein means at least one, or one or more, unless specified otherwise.

Specific and preferred values listed below for radicals, substituents, and ranges, are for illustration only; they do not exclude other defined values or other values within defined ranges for the radicals and substituents. The compounds of the disclosure include compounds of formula (I) and like compounds having any combination of the values, specific values, more specific values, and preferred values described herein.

Synthetic Methods

The compounds of formula (I)-(IV) are generally synthesized by reacting either oleic acid or activated derivatives thereof (e.g. N-oleoyloxysuccinimide or oleoyl chloride) with appropriate alcohols. Further process guidance is provided in the representative schemes and description below. The compounds, obtained after a suitable work-up and purification, are in the form of free bases or are subsequently converted into their pharmaceutically acceptable salts, e.g. HCl, mesylate, hemitartrate, etc.

Please note in Schemes 1-6 that R1 is

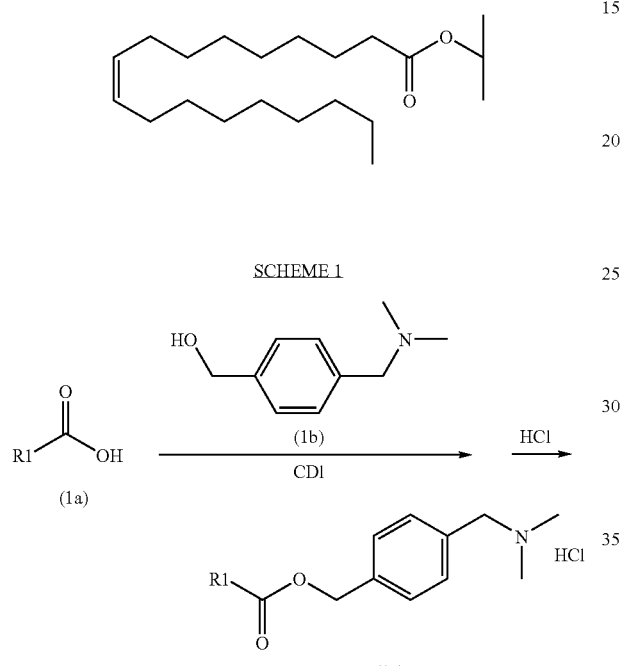

Octadec-(Z)-9-enoic acid 4-dimethylaminomethyl-benzyl ester HCl (1c)

N,N'-carbonyldiimidazole, (CDI, 1.22 g, 7.52 mmol) was added to a mixture of 90% oleic acid (1a), (1.24 g, 3.95 mmol) in acetonitrile (35 ml) while stirring at rt. The solution was stirred at 25° C. for 60 min under a nitrogen atmosphere, and 4-(dimethylamino)methyl-benzyl alcohol HCl salt (1b) (0.85 g, 4.21 mmol) was added. The mixture was heated at reflux for 24 hr, cooled to rt, and impregnated onto 3 g of silica. Purification was accomplished by flash column chromatography (eluting with chloroform/ethanol 95/5). Evaporation of solvents under reduced pressure and drying under vacuum at 60° C. gave 1.13 g (67%) of the free base as an oil.

The free base (1.13 g, 2.63 mmol) was dissolved in anhydrous ether (150 ml) and a solution of HCl gas in anhydrous ether (5 ml) was added. The turbid mixture was stirred at rt for 60 min, and the solvent was evaporated at reduced pressure. The gummy white solid was washed with dry ether (50 ml), and the ether was decanted off. The ether washing and decanting step was repeated (3×50 ml). The resulting residue was evaporated to dryness under vacuum, and then dried at 60° C. for 24 hr to give 0.92 g (75.4%) of octadec-(Z)-9-enoic acid 4-dimethylaminomethyl-benzyl ester HCl (1c) as a white solid, mp 145-146° C.

$^1$H NMR (δ, DMSO-$d_6$): 11.0 (br, 1H, exch.), 7.60-7.57 (d, 2H), 7.44-7.41 (d, 2H), 5.32 (m, 2H, vinyl), 5.12 (s, 2H, $C_6H_5$—$CH_2$—O), 4.26 (s, 2H, $C_6H_5$—$CH_2$—N), 2.66 (s, 6H, N($CH_3$)$_2$), 2.36 (t, 2H, $CH_2$—COOR), 2.00-1.97 (m, 4H, allyl), 1.57-1.53 (m, 2H, $CH_2$—$CH_2$—COOR), 1.26-1.24 (m, 20H), 0.87-0.83 (t, 3H, Me) ppm.

MS: 430 (MH$^+$, 100).

Microanal.: calcd. for $C_{28}H_{48}NClO_2$: C, 72.14; H, 10.38; N, 3.00; Cl, 7.61.

Found: C, 72.08; H, 10.50; N, 2.93; Cl, 7.54.

Octadec-(Z)-9-enoic acid 4-formyl-phenyl ester (2c)

A mixture of 4-hydroxybenzaldehyde (2b) (3.66 g, 30 mmol), dry acetonitrile (100 ml), potassium carbonate (8.29 g, 60 mmol), and 85% oleoyl chloride (2a) (10.62 g, 30 mmol) was stirred and heated at reflux under nitrogen for 24 hrs. The mixture was cooled to rt and filtered. The residue washed with acetonitrile (3×50 ml). The combined organic layer was evaporated to dryness under vacuum and purified by flash column chromatography (eluting with hexane/ethyl acetate 75/25), to give 3.4 g (29.3%) of octadec-(Z)-9-enoic acid 4-formyl-phenyl ester (2c) as a light yellow solid.

$^1$H NMR (CDCl$_3$, δ): 10.00 (s, 1H,CHO), 7.91 (d, 2H), 7.28-7.25 (d, 2H), 5.35 (m, 2H, vinyl), 2.61-2.56 (t, 2H, $CH_2$—COOR), 2.04-2.00 (m, 4H, allyl), 1.79-1.74 (m, 2H, $CH_2$—$CH_2$—COOR), 1.37-1.26 (m, 20H), 0.87 (t, 3H, Me) ppm.

Octadec-(Z)-9-enoic acid 4-dimethylaminomethyl-phenyl ester HCl (2d)

A mixture of dimethylamine hydrochloride (0.62 g, 7.60 mmol), sodium acetate (0.51 g, 6.15 mmol), and 95% sodium cyanoborohydride, (0.39 g, 5.87 mmol) was dissolved in dry methanol (40 ml), and the pH of the solution was adjusted to 7-8 by the addition of several drops of glacial acetic acid. The solution was stirred under nitrogen. A solution of octadec-(Z)-9-enoic acid 4-formyl-phenyl ester (2c) (1.50 g, 3.88 mmol) in dry methanol (15 ml) was added to the above solution. The mixture was stirred at rt under nitrogen for 24 hrs. Acetone (150 ml) was added and the solution was acidified to pH of 1 with 2N HCl. Solvents were removed at reduced pressure, and water (60 ml) was added. The mixture was extracted with methylene chloride (3×60 ml). The aqueous layer was made basic (pH 8-9) with aqueous ammonia, and the aqueous layer was extracted with methylene chloride (9×50 ml), and dried. Evaporation of the solvent at reduced pressure gave a crude product which was purified by flash column chromatography (eluting with chloroform/ethanol 95/5), to give 430 mg. (27%) of the free base as an oil.

The free base (0.43 mg, 1.04 mmol) was dissolved in anhydrous ether (60 ml) and a solution of HCl gas in anhydrous ether (2 ml) was added. The turbid mixture was stirred at rt for 60 min, and the solvent was evaporated at reduced pressure. The white solid was washed with dry ether (50 ml), and the ether was decanted off. The ether washing and decanting step was repeated (3×50 ml). The resulting residue was evaporated to dryness under vacuum, and dried under vacuum at 60° C. for 24 hrs to give 0.40 g (85%) of octadec-(Z)-9-enoic acid 4-dimethylaminomethyl-phenyl ester HCl (2d) as a white solid, mp 176-178° C.

$^1$H NMR (δ, DMSO-d$_6$): 11.0 (broad, 1H, exch.), 7.65-7.62 (d, 2H), 7.22-7.19 (d, 2H), 5.34 (m, 2H, vinyl), 4.27 (s, 2H, C$_6$H$_5$—CH$_2$—N), 2.67 (s, 6H, N(CH$_3$)$_2$), 2.58-2.54 (t, 2H, CH$_2$—COOR), 2.02-1.97 (m, 4H, allyl), 1.68-1.58 (m, 2H, CH$_2$—CH$_2$—COOR), 1.30-1.24 (m, 20H), 0.85 (t, 3H, Me) ppm.

MS: 416 (MH$^+$, 100).

Microanal.: calcd. for C$_{27}$H$_{46}$NClO$_2$: C, 71.73; H, 10.26; N, 3.10; Cl, 7.84.

Found: C, 71.98; H, 10.22; N, 2.98; Cl, 8.09.

SCHEME 3

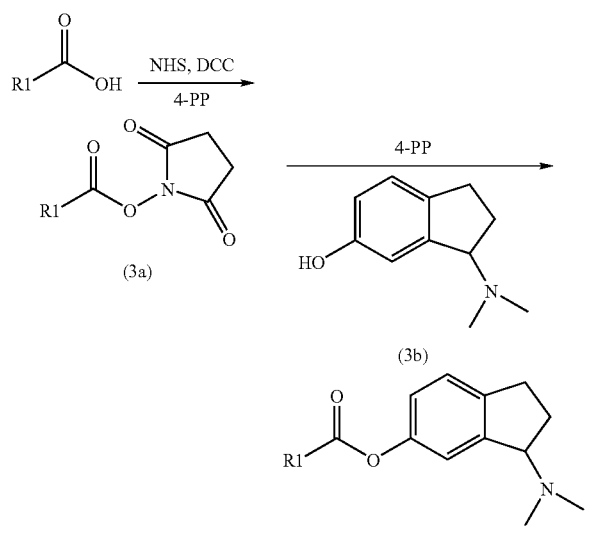

Octadec-(Z)-9-enoic acid-3-dimethylamino-indan-5-yl ester (3c)

N-Oleoyloxysuccinimide (3a) was prepared according to K. Vavrova et al., Bioorg. and Med. Chem., 11, 5386 (2003).

6-Hydroxy-N,N-dimethylaminoindan (3b) was prepared as described in J. Sterling et al., J. Med. Chem., 45, 5260-5279 (2002).

A solution of 6-hydroxy-N,N-dimethylaminoindan free base (3b) (0.434 g, 2.45 mmol), N-oleoyloxysuccinimide (3a) (0.90 g, 2.37 mmol), 4-pyrrolidinopyridine (4-PP, 0.39 g, 2.63 mmol), and dry DME (40 ml) was stirred and heated at 60° C. under nitrogen for 48 hr. The solvent was removed at reduced pressure, and the crude residue was purified by flash column chromatography using dichloromethane/methanol 90/10 to give 400 mg (38%) of the free base as an oil.

MS: 442 (MH$^+$, 100), 397 (9).

SCHEME 4

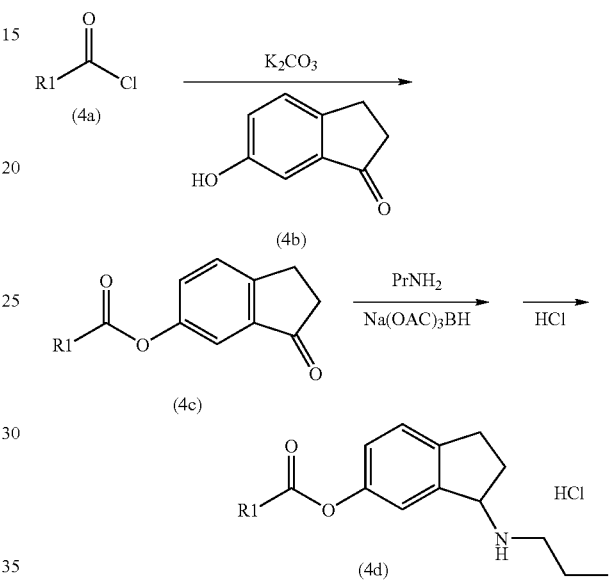

Octadec-(Z)-9-enoic acid 3-oxo-indan-5-yl ester (4c)

A mixture of 6-hydroxy-1-indanone (4b) (2.96 g, 20 mmol), dry acetonitrile (100 ml), potassium carbonate (5.53 g, 40 mmol), and 85% oleoyl chloride (4a), (7.08 g, 20 mmol) was stirred and heated at reflux under nitrogen for 24 hrs. The mixture was cooled to rt and filtered. The residue washed with acetonitrile (3×50 ml). The combined organic layer was evaporated to dryness under vacuum and purified by flash column chromatography (eluting with hexane/ethyl acetate 75/25), to give 4.4 g (53%) of octadec-(Z)-9-enoic acid 3-oxo-indan-5-yl ester (4c) as an off-white solid.

$^1$H NMR (CDCl$_3$, δ): 7.49-7.43 (m, 2H), 7.31-7.26 (m, 1H), 5.40-5.33 (m, 2H, vinyl), 3.15-2.71 (m, 4H, indanone), 2.59-2.54 (t, 2H, CH$_2$—COOR), 2.04-2.00 (m, 4H, allyl), 1.75-1.73 (m, 2H, CH$_2$—CH$_2$—COOR), 1.37-1.26 (m, 20H), 0.89-0.85 (t, 3H, Me) ppm.

Octadec-(Z)-9-enoic acid 3-propylamino-indan-5-yl ester HCl (4d)

Octadec-(Z)-9-enoic acid 3-oxo-indan-5-yl ester (4c) (0.95 g, 2.30 mmol) was dissolved in DCE (50 ml) and the solution was treated with n-propylamine (0.17 g, 2.88 mmol) and stirred at rt for 30 min. Sodium triacetoxyborohydride (0.80 g, 3.77 mmol) was then added, and the mixture was stirred at rt for 88 hr. Solvent was removed at reduced pressure to give a semi-solid residue which washed with ethyl acetate (5×50 ml). The ethyl acetate washings were filtered under vacuum, and the solvent was evaporated at reduced pressure. The residue was purified by flash column chromatography (eluting with dichloromethane/methanol 90/10) to give 400 mg (38%) of the free base as an off-white solid.

The free base (0.25 g, 0.55 mmol) was dissolved in dry ether (50 ml) and a solution of HCl gas in dry ether (2 ml) was added. The mixture was stirred at rt for 30 min, and solvent was evaporated under vacuum. The white solid washed with dry ether (50 ml), and collected by filtration. The residue was dried at 60° C. under vacuum for 40 hr to give 81 mg (30%) of octadec-(Z)-9-enoic acid 3-propylamino-indan-5-yl ester HCl (4d) as a white solid.

$^1$H NMR (DMSO-$d_6$): 9.6-9.2 (broad, 2H, exch.), 7.56 (br s, 1H), 7.38-7.35 (d, 1H), 7.11-7.07 (m, 1H), 5.36-5.33 (m, 2H, vinyl), 4.76-4.71 (m, 1H, C1-H), 3.14-3.07 (m, 1H,C3-H), 2.91-2.81 (m, 3H, N—CH$_2$—CH$_2$—CH$_3$, and C3-H'), 2.61-2.56 (t, 2H, CH$_2$—COOR), 2.49-2.42 (m, 1H, C2-H), 2.30-2.15 (m, 1H,C2-H'), 2.05-1.95 (broad, 4H, allyl), 1.80-1.58 (m, 4H, CH$_2$—CH$_2$—COOR, and N—CH$_2$—CH$_2$—CH$_3$), 1.38-1.20 (m, 20H), 0.93 (t, 3H, N—CH$_2$—CH$_2$—CH$_3$), 0.89-0.82 (t, 3H, Me) ppm.

MS: 456 (MH$^+$, 24), 397 (17), 245 (15), 135 (47), 133 (100).

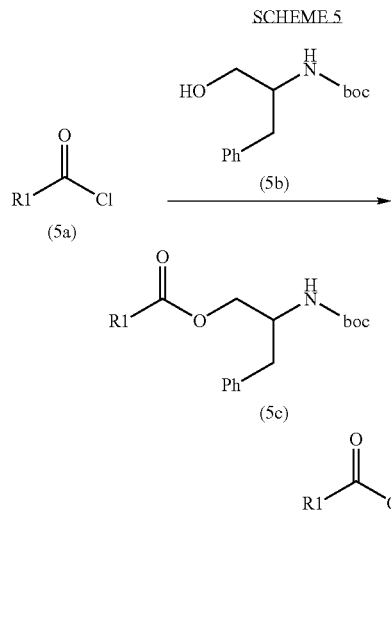

Octadec-(Z)-9-enoic acid 2-N-Boc-amino-3-phenyl-propyl ester (5c)

A mixture of Boc-L-phenylalaninol (5b) (2.51 g, 10 mmol), dry acetonitrile (50 ml), potassium carbonate (2.76 g, 20 mmol), and oleoyl chloride (5a) (85%), (3.54 g, 10 mmol) was stirred and heated at reflux under nitrogen for 24 hr. The mixture was cooled to rt and filtered. The cake washed with acetonitrile (3×50 ml). The combined organic layer was evaporated to dryness under vacuum and purified by flash column chromatography (hexane/ethyl acetate 75/25). Evaporation of solvents under reduced pressure and drying under vacuum gave 2.48 g (48%) of octadec-(Z)-9-enoic acid 2-N-Boc-amino-3-phenyl-propyl ester (5c) as an off-white solid.

$^1$H NMR (δ, DMSO-$d_6$): 7.32-7.25 (m, 2H), 7.20-7.15 (m, 3H), 6.90-6.85 (d, 1H, NHboc), 5.33 (m, 2H, olefinic protons), 4.00 (m, 1H, tertiary H), 3.87-3.82 (m, 2H, CO$_2$CH$_2$), 2.76-2.62 (m, 2H, CH$_2$—COOR), 2.27 (m, 2H, C$_6$H$_5$CH$_2$), 2.00-1.95 (m, 4H, CH$_2$-olefin-CH$_2$), 1.53-1.47 (m, 2H, CH$_2$—CH$_2$—COOR), 1.36-1.20 (m, 29H, oleic H and Boc protons), 0.87-0.83 (t, 3H, Me) ppm.

Octadec-(Z)-9-enoic acid 2-amino-3-phenyl-propyl ester HCl (5d)

Octadec-(Z)-9-enoic acid 2-N-Boc-amino-3-phenyl-propyl ester (5c) obtained above (1.25 g, 2.42 mmol) was dissolved in ethyl acetate (25 ml) and the solution was treated with 25 ml of 2N HCl in ethyl acetate (50 mmol). The mixture was stirred at rt for 24 hr, and evaporated to dryness under vacuum. The resulting viscous oil was dissolved by stirring in a 1:1 water/ether mixture (100 ml). The aqueous layer was separated, and the ether layer was re-extracted with water (2×25 ml). The combined aqueous layers were carefully evaporated to dryness at reduced pressure, and the resulting oil was dried to give 0.95 g (86%) of octadec-(Z)-9-enoic acid 2-amino-3-phenyl-propyl ester HCl (5d) as a waxy off-white solid.

$^1$H NMR (δ, DMSO-$d_6$): 8.50-8.30 (br, 3H, exch.) 7.37-7.32 (m, 2H), 7.29-7.25 (m, 3H), 5.33 (m, 2H, olefinic protons), 4.13-3.93 (m, 2H, CO$_2$CH$_2$), 3.70-3.60 (m, 1H, tertiary H), 3.09-2.78 (m, 2H, CH$_2$—COOR), 2.33 (m, 2H,C$_6$H$_5$CH$_2$), 2.02-1.95 (m, 4H, CH$_2$— olefin-CH$_2$), 1.53-1.47 (m, 2H, CH$_2$—CH$_2$—COOR), 1.30-1.20 (m, 20H, oleic H), 0.87-0.82 (t, 3H, Me) ppm.

MS: 416 (MH$^+$, 100), 117 (77).

Microanalysis: calculated for $C_{27}H_{46}NClO_2$: C, 71.73; H, 10.26; N, 3.10: Cl, 7.84.

Found: C, 71.15; H, 10.37; N, 3.03: Cl, 7.55.

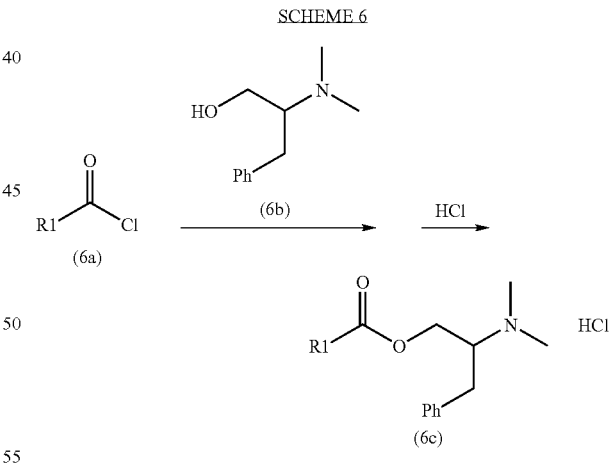

2-Dimethylamino-3-phenyl-1-propanol (6b)

2-amino-3-phenyl-1-propanol (1.0 g, 6.61 mmol) was added to 90% formic acid (1.69 g, 33.05 mmol), and 37% aqueous formaldehyde (1.49 ml, 19.83 mmol). The clear solution was stirred and heated at 95-100° C. for 21 hr under nitrogen. The mixture was cooled to rt, and acidified to pH 1 with 2N HCl. Evaporation to dryness followed by the addition of ether (40 ml) and water (40 ml) gave two layers after vigorous stirring. The layers were separated, and the organic layer was re-extracted with water (3×75 ml). The combined water layers were brought to pH 8-9 by the addition of $NH_4OH$ solution, and extracted with $CH_2Cl_2$ (40 ml). The layers were separated, and the aqueous layer was re-extracted with $CH_2Cl_2$ (8×40 ml). The combined organic layers were dried and evaporated to dryness under vacuum to give 1.0 g (84%) of 2-dimethylamino-3-phenyl-1-propanol (6b) as an off-white solid.

$^1$H NMR ($\delta$, $CDCl_3$): 7.32-7.26 (m, 2H), 7.23-7.13 (m, 3H), 3.85-3.78 (br s, 1H, tertiary H), 3.55-3.33 (m, 2H, $CH_2OH$), 2.98-2.90 (m, 2H,$C_6H_5CH_2$), 2.42 (s, 6H, $N(CH_3)_2$), 2.39-2.31 (m, 1H, OH) ppm.

Octadec-(Z)-9-enoic acid 2-dimethylamino-3-phenyl-propyl ester HCl (6c)

A mixture of 2-dimethylamino-3-phenyl-1-propanol (6b) (0.95 g, 5.30 mmol), dry acetonitrile (35 ml), potassium carbonate (1.46 g, 10.60 mmol), and oleoyl chloride (6a) (85%) (1.88 g, 5.30 mmol) was stirred and heated at reflux under nitrogen for 24 hr. The mixture was cooled to rt and filtered. The cake washed with acetonitrile (3×30 ml). The combined organic layer was evaporated to dryness under vacuum and purified by flash column chromatography (ethyl acetate). Evaporation of solvents under reduced pressure and drying under vacuum gave 1.67 g (71%) of the free base as a yellow oil.

The free base (1.67 g, 3.76 mmol) was dissolved in dry ether (30 ml) and a solution of HCl gas in dry ether (5 ml) was added. The mixture was stirred rt for 30 min, and solvent was evaporated under vacuum, to give 1.77 g (98% g) of octadec-(Z)-9-enoic acid 2-dimethylamino-3-phenyl-propyl ester HCl (6c) as a viscous oil.

$^1$H NMR ($\delta$, DMSO-$d_6$): 11.13 (br, 1H, exch), 7.40-7.20 (m, 5H), 5.34 (m, 2H, olefinic protons), 4.22-4.03 (m, 2H, $CO_2CH_2$), 3.90-3.80 (m, 1H, tertiary H), 3.62-3.28 (m, 2H,$CH_2$—COOR), 2.90-2.80 (m, 6H, $N(CH_3)_2$), 2.33 (m, 2H, $C_6H_5CH_2$), 2.02-1.92 (m, 4H, allyl), 1.53-1.47 (m, 2H, $CH_2$—$CH_2$—COOR), 1.32-1.18 (m, 20H, oleic H), 0.87-0.82 (t, 3H, Me) ppm.

MS: 444 (MH+, 100), 399 (34), 180 (9), 162 (28).

Microanalysis: calculated for a hydrate (containing 1 mole of water), $C_{29}H_{52}NClO_3$: C, 69.92; H, 10.52; N, 2.81; Cl, 7.12.

Found: C, 70.00; H, 10.45; N, 2.84; Cl, 7.76.

Pharmaceutical Compositions

The present invention further provides a pharmaceutical composition which comprises a therapeutically effective amount of a compound of formula (I)-(IV) or a pharmaceutically acceptable salt thereof and a pharmaceutically acceptable carrier. The "therapeutically effective amount" of a compound of formula (I)-IV) or a pharmaceutically acceptable salt thereof may be determined according to methods well known to those skilled in the art, indications of such amounts are given below.

The pharmaceutical composition provided by the present invention may be in solid, semisolid or liquid form and may further include pharmaceutically acceptable fillers, carriers or diluents, and other inert ingredients and excipients. The composition can be administered by any suitable route such as, but not limited to, oral, topical, or parenteral e.g. by injection through subcutaneous, intravenous, intramuscular, or any other suitable route.

Generally, the formulations are prepared by contacting the compounds of the present invention each uniformly and intimately with liquid carriers or finely divided solid carriers or both. Then, if necessary, the product is shaped into the desired formulation. These preparations can be made by conventional methods known to those skilled in the art, for example as described in "Remington's Pharmaceutical Science", A. R. Gennaro, ea., 17th edition, 1985, Mack Publishing Company, Easton, Pa., USA.

Pharmaceutical compositions for topical application take the form of creams, milks, gels, dispersion or microemulsions, lotions thickened to a greater or lesser extent, impregnated pads, ointments or sticks, or alternatively the form of aerosol formulations in spray or foam form or alternatively in the form of a cake of soap. Non-aqueous vehicles such as fixed oils can be also useful, as well as liposomes.

For parenteral administration, the compounds may be formulated by mixing; each at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. In one embodiment, the carrier is a parenteral carrier which is a solution that is isotonic with the blood of the recipient. Examples of such carrier vehicles include water, saline, Ringer's solution, and dextrose solution.

If given continuously, the compounds of the present invention are each typically administered by 1-4 times per day. The dosage will depend of the state of the patient and severity of the disease and will be determined as deemed appropriate by the practitioner.

Methods of Treatment

The present invention further provides treatment of inflammatory disorders with a compound of formula (I) or a pharmaceutical composition comprising a therapeutically effective amount of a compound of formula (I) or a pharmaceutically acceptable salt thereof, and a pharmaceutically acceptable carrier.

The immune system, in both its innate and adaptive arms, is involved in regulating inflammation of every type, and inflammation is a key factor in processes such as wound healing, connective tissue re-modeling, angiogenesis, organ regeneration, neuroprotection, as well as in the adaptive immune responses seen in autoimmunity, allergies, graft rejection, and infection. Therefore, anti-inflammatory agents that modulate the inflammatory response such as those described here will be useful in a variety of conditions.

Inflammatory disorders that can be treated with the immunomodulators of the present invention include, but are not limited to, immunologically-mediated chronic or acute inflammatory disorders selected from an autoimmune disease, severe allergies, asthma, graft rejection or for the treatment of chronic degenerative diseases such as Alzheimer's disease, and in neuroprotection, organ regeneration, chronic ulcers of the skin, and schizophrenia.

Examples of autoimmune diseases that can be treated according to the invention are multiple sclerosis or a human arthritic condition, e.g. rheumatoid arthritis, reactive arthritis with Reiter's syndrome, ankylosing spondylitis and other inflammations of the joints mediated by the immune system. Other autoimmune diseases are contemplated and are presented in the following list in the context of the organ or tissue involved. Thus, according to the invention, the immunologically mediated inflammatory disorder may be myasthenia gravis, Guillain-Barre syndrome, and other inflammatory diseases of the nervous system; psoriasis, pemphigus vulgaris and other diseases of the skin; systemic lupus erythematosus, glomerulonephritis and other diseases affecting the kidneys; atherosclerosis and other inflammations of the blood vessels; autoimmune hepatitis, inflammatory bowel diseases, e.g. Crohn's disease, pancreatitis, and other conditions of the gastrointestinal system; type 1 diabetes mellitus (insulin-dependent diabetes mellitus or IDDM), autoimmune thyroiditis (Hashimoto's thyroiditis), and other diseases of the endocrine system.

The present invention will be illustrated by the following examples, which should not be considered to limit the scope of the invention.

EXAMPLE

Inhibition of DTH Skin Reactions

Delayed type hypersensitivity (DTH), a localized inflammatory reaction induced by cytokines secreted by $T_H$ cells when they encounter certain types of antigens, is an established experimental model for skin inflammation.

DTH reactions were induced in the abdomen skin of 8 week old female Balb/c mice. The mice were sensitized first by topical application of 100 μl of a 5% Oxazolone (4-Ethoxymethylene-2-phenyl-2-oxazolin-5-one; Sigma) solution in ethanol/acetone (3:1, vol/vol) to a shaved abdomen. The mice were anesthetized with ip injection of Ketamine (1 ml)+Xylazine (1 ml)+Saline (8 ml), (0.2 ml per 20 g mouse). Anesthetization was performed before the shaving of the abdomen and the first sensitization.

After 4 days the mice were challenged for the second time using 1% Oxazolone (4-Ethoxymethylene-2-phenyl-2-oxazolin-5-one; Sigma) solution in ethanol/acetone (3:1, vol/vol). The solution was pipetted to the shaved abdomen of the mice.

Six days after the first sensitization, the right ear of each mouse was challenged with a topical application of 20 μl (10 μl on each surface of the ear) of a 1% Oxazolone solution in olive oil/acetone (3:1, vol/vol).

Treatment was given 30 min after challenging by applying 40 μl (20 μl on each surface of the ear) of treatment compounds on the challenged ear of each mouse.

After 24 hours, the extent of inflammation was measured using the mouse ear swelling test (caliper) and the percent inhibition induced by the treatment was quantified.

The experiment includes groups treated with 5, 15, 40, and 100 mg/ml of octadec-(Z)-9-enoic acid 4-dimethylaminomethyl-benzyl ester HCl (1c) and groups treated with 5, 15, 40, and 100 mg/ml of octadec-(Z)-9-enoic acid 4-dimethylaminomethyl-phenyl ester HCl (2d). The experiment also includes dexamethasone (2 mg/mouse) as a positive control, one negative control group (PBS, phosphate buffered saline), and one naïve group. There were 6 mice per group. The researchers who performed the measurements were blinded as to the grouping of each mouse. Results of the experiment are presented below in Table 1.

TABLE 1

| Compound | treatment (mg/ml) | Dose (mg/ mouse) | Diff. (mm) | % Inf | % Inhibit |
| --- | --- | --- | --- | --- | --- |
| PBS |  |  | 0.27 | 128.52 | 0.00 |
| 1c | 5 | 0.2 | 0.20 | 92.65 | 26.74 |
|  | 15 | 0.6 | 0.20 | 103.21 | 26.01 |
|  | 40 | 1.6 | 0.12 | 58.56 | 54.82 |
|  | 100 | 4 | 0.10 | 48.19 | 63.37 |

TABLE 1-continued

| Compound | treatment (mg/ml) | Dose (mg/ mouse) | Diff. (mm) | % Inf | % Inhibit |
| --- | --- | --- | --- | --- | --- |
| 2d | 5 | 0.2 | 0.24 | 113.46 | 13.31 |
|  | 15 | 0.6 | 0.22 | 107.18 | 21.25 |
|  | 40 | 1.6 | 0.24 | 114.66 | 13.31 |
|  | 100 | 4 | 0.11 | 55.96 | 59.10 |
| Positive control |  | 2 | 0.04 | 20.55 | 84.74 |
| Naïve |  |  | 0.01 | 3.14 | 98.17 |

In Table 1, "diff" refers to average difference between baseline and post treatment measurements in mm; "% Inf" refers to the (diff/baseline measurement)×100; and, "% Inhibit" refers to [1−(diff/diff of PBS)]×100. Baseline measurements of the ear were conducted before the first sensitization.

Octadec-(Z)-9-enoic acid 4-dimethylaminomethyl-benzyl ester HCl (1c) and octadec-(Z)-9-enoic acid 4-dimethylaminomethyl-phenyl ester HCl (2d) were effective in the DTH skin reaction model. The most effective doses (in mg/ml) were 40 and 100 for octadec-(Z)-9-enoic acid 4-dimethylaminomethyl-benzyl ester HCl (1c) and 100 for octadec-(Z)-9-enoic acid 4-dimethylaminomethyl-phenyl ester HCl (2d).

The above specification, examples and data provide a complete description of the compounds of the invention, manufacture of the compounds and composition including the compounds of the invention and use of the compounds and composition including the compounds of the invention. Since many embodiments of the invention can be made without departing from the spirit and scope of the invention, the invention resides in the claims hereinafter appended.

The invention claimed is:

1. A compound of the formula (I):

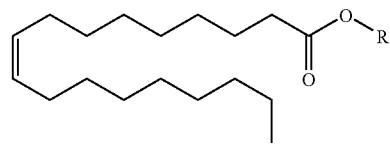

wherein R is either:

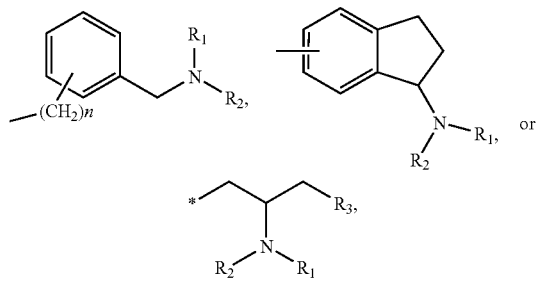

$R_1$ and $R_2$ are the same or different and are either hydrogen or $C_1$-$C_4$ alkyl, n is 0 or 1, and $R_3$ is unsubstituted phenyl or phenyl substituted with alkyl, alkoxy, hydroxyl, halogen;

or a pharmaceutically acceptable salt thereof.

2. The compound of claim 1, wherein R is

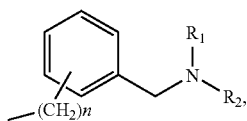

and $R_1$ and $R_2$ are each methyl, n is as defined above; or a pharmaceutically acceptable salt thereof.

3. The compound of claim 2, wherein the compound is octadec-(Z)-9-enoic acid 4-dimethylaminomethyl-benzyl ester or a pharmaceutically acceptable salt thereof.

4. The compound of claim 3, wherein the compound is octadec-(Z)-9-enoic acid 4-dimethylaminomethyl-benzyl ester HCl.

5. The compound of claim 2, wherein the compound is octadec-(Z)-9-enoic acid 4-dimethylaminomethyl-phenyl ester or a pharmaceutically acceptable salt thereof.

6. The compound of claim 5, wherein the compound is octadec-(Z)-9-enoic acid 4-dimethylaminomethyl-phenyl ester HCl.

7. The compound of claim 1, wherein R is

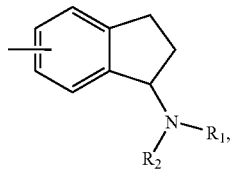

wherein $R_1$ and $R_2$ are as defined above, or a pharmaceutically acceptable salt thereof.

8. The compound of claim 7, wherein the compound is octadec-(Z)-9-enoic acid-3-dimethylamino-indan-5-yl ester or a pharmaceutically acceptable salt thereof.

9. The compound of claim 8, wherein the compound is octadec-(Z)-9-enoic acid-3-dimethylamino-indan-5-yl ester HCl.

10. The compound of claim 7, wherein the compound is octadec-(Z)-9-enoic acid 3-propylamino-indan-5-yl ester or a pharmaceutically acceptable salt thereof.

11. The compound of claim 10, wherein the compound is octadec-(Z)-9-enoic acid 3-propylamino-indan-5-yl ester HCl.

12. The compound of claim 1, wherein R is

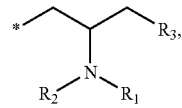

wherein $R_1$ and $R_2$ are as defined above and $R_3$ is unsubstituted phenyl, or a pharmaceutically acceptable salt thereof.

13. The compound of claim 12, wherein $R_1$ and $R_2$ are each hydrogen, or a pharmaceutically acceptable salt thereof.

14. The compound of claim 12, wherein $R_1$ and $R_2$ are each methyl, or a pharmaceutically acceptable salt thereof.

15. The compound of claim 13, wherein the compound is the hydrochloride salt.

16. The compound of claim 14, wherein the compound is the hydrochloride salt.

17. A pharmaceutical composition comprising the compound of claim 1 or a pharmaceutically acceptable salt thereof and a pharmaceutically acceptable carrier.

18. The pharmaceutical composition of claim 17, wherein the pharmaceutical composition is for topical administration.

19. A method of treating skin inflammation comprising administering a pharmaceutical composition of claim 17 to a subject in need thereof.

20. The method of claim 19, wherein the pharmaceutical composition is for topical administration.

21. A method of treating a subject suffering from a disorder selected from psoriasis, alopecia areata, pemphigus vulgaris, contact dermatitis, atopic dermatitis, vitiligo or inflammatory skin disorders comprising administering the pharmaceutical composition of claim 17 effective to treat the disorder in the subject.

* * * * *